US008808669B2

(12) United States Patent
Muthusamy et al.

(10) Patent No.: US 8,808,669 B2
(45) Date of Patent: Aug. 19, 2014

(54) GASTRORETENTIVE, EXTENDED RELEASE COMPOSITION OF THERAPEUTIC AGENT

(75) Inventors: Ramesh Muthusamy, Pune (IN); Mohan Gopalkrishna Kulkarni, Pune (IN)

(73) Assignee: Council of Scientific & Industrial Research (IN)

( * ) Notice: Subject to any disclaimer, the term of this patent is extended or adjusted under 35 U.S.C. 154(b) by 49 days.

(21) Appl. No.: 13/608,994

(22) Filed: Sep. 10, 2012

(65) Prior Publication Data

US 2013/0004434 A1    Jan. 3, 2013

Related U.S. Application Data

(63) Continuation of application No. PCT/IN2011/000156, filed on Mar. 9, 2011.

(30) Foreign Application Priority Data

Mar. 9, 2010   (IN) .......................... 0530/DEL/2010

(51) Int. Cl.
| | | |
|---|---|---|
| *A61K 47/34* | (2006.01) | |
| *A61K 31/496* | (2006.01) | |
| *A61K 31/5383* | (2006.01) | |
| *A61K 31/554* | (2006.01) | |
| *A61P 31/04* | (2006.01) | |
| *A61P 9/00* | (2006.01) | |
| *A61P 3/02* | (2006.01) | |
| *A61K 31/675* | (2006.01) | |
| *A61K 47/38* | (2006.01) | |
| *A61K 31/545* | (2006.01) | |
| *A61K 9/20* | (2006.01) | |
| *A61K 9/00* | (2006.01) | |
| *A61K 31/525* | (2006.01) | |

(52) U.S. Cl.
CPC ............ *A61K 9/0065* (2013.01); *A61K 31/5383* (2013.01); *A61K 31/545* (2013.01); *A61K 9/2031* (2013.01); *A61K 9/2054* (2013.01); *A61K 31/496* (2013.01); *A61K 31/554* (2013.01); *A61K 31/525* (2013.01); *A61K 9/2027* (2013.01)
USPC ......................................................... 424/44

(58) Field of Classification Search
None
See application file for complete search history.

(56) References Cited

U.S. PATENT DOCUMENTS

| 4,735,804 A | 4/1988 | Caldwell et al. |
| 5,002,772 A | 3/1991 | Curatolo et al. |
| 5,582,837 A | 12/1996 | Shell |
| 5,972,389 A | 10/1999 | Shell et al. |
| 6,207,197 B1 | 3/2001 | Illum et al. |
| 6,488,962 B1 | 12/2002 | Berner et al. |
| 6,548,083 B1 | 4/2003 | Wong et al. |
| 6,723,340 B2 | 4/2004 | Gusler et al. |
| 2001/0046473 A1 | 11/2001 | Besse |
| 2006/0013876 A1 | 1/2006 | Lohray et al. |
| 2009/0285865 A1 | 11/2009 | Shalaby |

FOREIGN PATENT DOCUMENTS

| EP | 1235557 B1 | 9/2002 |
| EP | 1745775 A1 | 1/2007 |
| WO | 2006063858 A1 | 6/2006 |
| WO | 2008010690 A1 | 1/2008 |
| WO | 2008074108 A2 | 6/2008 |
| WO | 2010103365 A2 | 9/2010 |

OTHER PUBLICATIONS

Rüdiger Gröning, Michael Berntgen, Manolis Georgarakis, "Acyclovir Serum Concentrations Following Peroral Administration of Magnetic Depot Tablets and the Influence of Extracorporal Magnets to Contril Gastrointestinal Transit"; European Journal of Pharmaceutics and Biopharmaceutics, 46, pp. 285-291, 1998.

Mahesh Chavanpatil, Paras Jain, Sachin Chaudhari, Rajesh Shear and Pradeep Vavia, "Developement of Sustained Release Gastroretentive Drug Delivery System for Oflaxacin: in Vitro and in Vivo Evaluation"; International Journal of Pharmaceutics, 304, pp. 178-184, 2005.

Mia Säkkinen, Janne Marvola, Hanna Kanerva, Kai Lindevall, Maija Lipponen, Tommi Kekki, Aapo Ahonen and Martti Marvola, "Gamma Scintigraphic Evaluation of the Fate of Microcrystalline Chitosan Granules in Human Stomach"; European Journal of Pharmaceutics and Biopharmaceutics, 57, pp. 133-143, 2004.

Jun Chen, William E. Blevins, Haesun Park, and Kinam Park, "Gastric Retention Properties of Superporous Hydrogel Composites"; Journal of Controlled Release, 64, pp. 39-51, 2000.

Zhepeng Liu, Weiyue Lu, Lisheng Qian, Xuhui Zhang, Pengyun Zeng and Jun Pan, "In Vitro and in Vivo Studies on Mucoadhesive Microspheres of Amoxicillin"; Journal of Controlled Release, 102, pp. 135-144, 2005.

F. Atyabi, H.L. Sharma, H.A.H. Mohammad and J.T. Fell, "In vivo Evaluation of a Novel Gastric Retentive Formulation based on Ion Exchange Resins"; Journal of Controlled Release, 42, pp. 105-113, 1996.

(Continued)

*Primary Examiner* — Suzanne Ziska
*Assistant Examiner* — Thurman Wheeler
(74) *Attorney, Agent, or Firm* — St. Onge Steward Johnston & Reens LLC

(57) ABSTRACT

A gastroretentive, extended release composition which floats and swells at acidic pH prevalent in the stomach. The composition includes a pH dependent graft copolymer, a gellable polymer, a therapeutic agent, a gas generating system and pharmaceutically acceptable ingredients. The disclosed composition is useful to deliver the therapeutic agent within the stomach for an extended period of time.

16 Claims, 6 Drawing Sheets

(56) References Cited

OTHER PUBLICATIONS

M. Cuña, M.J. Alonsoa and D. Torres, "Preparation and in Vivo Evaluation of Mucoadhesive Microparticles Containing Amoxycillin-Resin Complexes for Drug Delivery to the Gastric Mucosa"; European Journal of Pharmaceutics and Biopharmaceutics, 51, pp. 199-205, 2001.

Mia Säkkinen, Janne Marvola, Hanna Kanerva, Kai Lindevall, Aapo Ahonen and Martti Marvola, "Scitigraphic Verification of Adherence of Chitosan Formulation to the Human Oesophagus"; European Journal of Pharmaceutics and Biopharmaceutics, 57, pp. 145-147, 2004.

Chen, et al.; "Development of swelling/floating gastroretentive drug delivery system based on a combination of hydroxyethyl cellulose and sodium carboxymethyl cellulose for Losartan and its clinical relevance in healthy volunteers with CYP2C9 polymorphism"; European Journal of Pharmaceutical Sciences 39 (2010) 82-89.

Bardonnet, et al.; "Gastroretentive dosage forms: overview and special case of *Helicobacter pylori*"; Journal of Controlled Release 111 (2006) 1-18.

Jang, et al, "Gastroretentive drug delivery system of DA-6034, a new flavonoid derivative, for the treatment of gastritis"; International Journal of Pharmaceutics 356 (2008) 88-94.

International Preliminary Report on Patentability Application No. PCT/IN2011/000156 Completed: Jun. 25, 2012 17 pages.

International Search Report and Written Opinion of the International Searching Authority Application No. PCT/IN2011/000156 Completed: Nov. 23, 2011; Mailing Date: Nov. 30, 2011 13 pages.

Liu, et al.; "Zero-order delivery of a highly soluble, low dose drug alfuzosin hydrochloride via gastro-retentive system."; International Journal of Pharmaceutics 348 (2008) 27-34.

GASTRORETENTIVE, EXTENDED RELEASE COMPOSITION OF THERAPEUTIC AGENT

CROSS-REFERENCE TO RELATED APPLICATIONS

The present application is a continuation of pending International patent application PCT/IN2011/000156 filed on Mar. 9, 2011 which designates the United States and claims priority from Indian patent application 530/DEL/2010 filed on Mar. 9, 2010, the content of which is incorporated herein by reference.

FIELD OF THE INVENTION

The present invention relates to a gastroretentive, extended release composition that is retained in the stomach and releases the drug for an extended period of time.

BACKGROUND OF THE INVENTION

Sustained release formulations overcome the need for frequent administration of drug which enhance patient compliance and reduce drug toxicity. Since all drugs can not be absorbed throughout the gastrointestinal tract, they have to be targeted to the specific site where the absorption is more. Conventional enteric polymers suppress the release of drugs in stomach where the pH is acidic and release the drugs in near neutral or alkaline medium, prevalent in the intestinal region either immediately or in a sustained manner. The reverse enteric polymers can release the drug in stomach immediately and the release can not be sustained in view of the short residence of the dosage form in stomach. Gastroretentive drug delivery systems are needed for the delivery of drugs, which are better absorbed in the gastric region, have poor solubility in the intestinal region and/or are degraded by the enzymes present in intestine.

Gastroretentive dosage forms were developed by using various approaches in the past. One such approach was based on the mucoadhesive polymers. Ilium et el. disclosed in U.S. Pat. No. 6,207,197 B1 a bioadhesive formulation for the treatment of gastric ulcer caused by *Helicobacter pylori*. It comprised a drug core coated with rate controlling water insoluble polymer layer of ethylcellulose followed by bioadhesive outer layer of chitosan which was crosslinked with glutaraldehyde. The formulation was capable of adhering onto the gastric mucosa and releases the drug for an extended period of time within the stomach. Yeon et al. disclosed in WO2008/010690 A1 a bioadhesive composition which comprised multiple numbers of pellets coated with metformin hydrochloride followed by a bioadhesive polymer such as sodium alginate, sodium carboxymethyl cellulose, hydroxylpropylmethyl cellulose and chitosan. The pellets could be filled in the capsule or compressed into tablet along with the immediate release pellets which comprised glimepiride. WO2008/074108 A2 discloses a bioadhesive composition for the treatment of diabetes mellitus. It was prepared by wet granulating the mixture of metformin hydrochloride, bioadhesive polymer crosslinked polyacrylic acid and other ingredients and compressing the granules to form a tablet. The tablet was coated with a film forming hydrophilic polymer and glimepiride. The gelling behaviour of crosslinked polyacrylic acid led to adhesion of the dosage form to the gastric mucosa.

Mucoadhesive microspheres were developed by Liu et al. (Zhepeng Liu, Weiyue Lu, Lisheng Qian, Xuhui Zhang, Pengyun Zeng and Jun Pan, Journal of Controlled Release, 102, 135, 2005) for the treatment of gastric and duodenal ulcers associated with *Helicobacter pylori*. The microspheres were prepared by emulsification and evaporation method. Ethylcellulose was dissolved in acetone and the powder of crosslinked polyacrylic acid and the antibiotic amoxicillin were added and blended. The blend was dispersed in the light paraffin oil to form microspheres. Similar microspheres were prepared without using bioadhesive polymer as a control.

Cuña et al. developed mucoadhesive particles comprising complex of drug and anion exchange resin (M. Cuña, M. J. Alonsoa and D. Tones, European Journal of Pharmaceutics and Biopharmaceutics, 51, 199, 2001). The complex was prepared by dispersing the anion exchange resin particles in the aqueous medium containing amoxicillin. The complex formed was suspended in a dispersion of bioadhesive polymer, crosslinked polyacrylic acid and then emulsified in liquid paraffin. Gastric retention of the bioadhesive particles was evaluated in rats and the results showed that almost all the particles left the stomach within 2-3 hours. It was concluded that the mucoadhesive polymer could not enhance the gastric residence time.

Säkkinen et al. described a mucoadhesive gastro-retentive drug delivery system based on microcrystalline chitosan (Mia Säkkinen, Tiina Tuononen, Heidi Jürjenson, Peep Veski and Martti Marvol, European Journal of Pharmaceutical Sciences, 19, 345, 2003). In vivo study on human volunteers showed that the formulations did not adhere onto the gastric mucosa and they were passed onto the intestinal region. The result was further confirmed by gamma scintigraphy study (Mia Säkkinen, Janne Marvola, Hanna Kanerva, Kai Lindevall, Maija Lipponen, Tommi Kekki, Aapo Ahonen and Martti Marvola, European Journal of Pharmaceutics and Biopharmaceutics, 57, 133, 2004). Also the potential risk of oesophagus adhesion of chitosan particles was found by Säkkinen et al. (Mia Säkkinen, Janne Marvola, Hanna Kanerva, Kai Lindevall, Aapo Ahonen and Martti Marvola, European Journal of Pharmaceutics and Biopharmaceutics, 57, 145, 2004).

As described in the above disclosures the mucoadhesive gastroretentive delivery systems are not reliable as the adhesion to gastric mucosa is unpredictable. The adhesive property of polymers was affected due to their interaction with biological components present in the stomach. Also it was found that the adhesive strength was not adequate to withstand the mechanical action caused by the presence of food in the stomach.

Another approach to attain gastric retention was keeping the dosage form away from the pylorus valve. This was achieved by making the dosage form which can float on the gastric fluid. Such a floating dosage form was disclosed by Besse in US 200110046473 A1 which comprised a drug, a hydrophilic polymer like hydroxypropylmethyl cellulose and gas generating agent. The floating tablet was prepared by mixing the said components and other ingredients and then compressing into the tablet. Mahendra et al. disclosed in EP 1745775 A1 a floating dosage form which comprised a drug, a weak gelling polymer like sodium carboxymethyl cellulose, a strong gelling polymer like hydroxypropylmethyl cellulose, gas generating agent and other ingredients. Similarly, Chavanpatil et al. (Mahesh Chavanpatil, Paras Jain, Sachin Chaudhari, Rajesh Shear and Pradeep Vavia, International Journal of Pharmaceutics, 304, 178, 2005), Lohray et al. in US 2006/0013876 and Pascal et al in WO2006/063858 disclose floating dosage form variants with and without gas generating agents and low density buoyant particle composition respectively.

Atyabi et al. described floating microcapsules as a gastroretentive drug delivery system (F. Atyabi, H. L. Sharma, H. A. H. Mohammad and J. T. Fell, Journal of Controlled Release, 42, 105, 1996). The microcapsules were based on the ion exchange resin which comprised sodium bicarbonate and an anionic inorganic compound sodium pertechnetate as a model drug. The capsules were coated with Eudragit RS which helped to retain the generated gas within the microcapsules. The gastric retention of coated and uncoated microcapsules was compared and the results showed that the coated capsules could float on the gastric fluid for longer duration than uncoated microcapsules. However, the system is limited to only ionic drugs as they are capable forming ionic complex with oppositely charged resin beads.

The major draw back associated with floating dosage form is that they require fluid in the stomach. When the stomach gets emptied by gastric motility, there is no fluid in the stomach on which the dosage could float. Numerous dosage forms were developed which could be retained in the stomach even after gastric motility action. These dosage forms were designed in such way that their dimensions were larger than opened pylorus. Such dosage forms could be folded to small size and then filled into capsule for ease of administration. The expansion of dosage forms into large dimension occurred once they were placed in the gastric fluid as disclosed in U.S. Pat. Nos. 4,735,804, 5,002,772 and EP 1235557.

Although, numerous expandable dosage forms have been developed for gastroretentive drug delivery, their reliability and safety is still a matter of concern. For example premature expansion of delivery device before reaching the stomach may lead to oesophagal obstruction. Also the failure of the device to expand may result in emptying of the dosage form from the stomach. This may lead to obstruction and injuries in the intestinal tract. Another problem associated with these systems is storage in the folded form, as it reduces the resilience and limits rapid unfolding in the gastric fluid. The construction of these devices, is difficult and needs special equipments.

Gröning et al. (Rüdiger Gröning, Michael Berntgen, Manolis Georgarakis, European Journal of Pharmaceutics and Biopharmaceutics, 46, 285, 1998) described a magnetic depot tablet system for gastroretentive drug delivery. It comprised a circular magnet coated with three layers one over another comprising carnauba wax layer, an inner layer comprising the major portion of drug, hydroxypropylmethyl cellulose and magnesium stearate followed by an outer layer comprising minor portion of the drug, hydroxypropylmethyl cellulose, lactose and magnesium stearate. In-vivo study was conducted in human volunteers by administering them with the magnetic depot tablets.

The movement of tablets was controlled by an external magnet which was fixed on the subject body. The results showed that the dosage forms retained in the stomach for 12 hours and released the content. However, the practical utility of the system is limited, since the patient needs to carry an external magnet to manipulate the location of the magnetic depot tablet.

Chen et at (Jun Chen, William E. Blevins, Haesun Park, and Kinam Park, Journal of Controlled Release, 64, 39, 2000) described a superporous hydrogel composition for gastroretentive drug delivery. The delivery system was based on the copolymer of acrylamide and sulfopropyl acrylate crosslinked with methylenebisacrylamide. The hydrogel was prepared in the presence of gas generating agent and other ingredients with porous structure. The hydrogel swelled into large size within a shorter period of time. In-vivo studies were conducted in dogs and the results showed that the hydrogels were retained in the stomach upto 32 hours but fragmented in between 27 and 32 hours. However, the loading of the drug within the hydrogel system and its release behaviour was not reported.

Wong et al, disclosed in U.S. Pat. No. 6,548,083 B1 a gastroretentive drug delivery system which swelled to large size upon contacting with simulated gastric fluid. It was prepared by granulating the mixture of active agent, water soluble polymer, water insoluble polymer and other ingredients and then compressing into the caplet shaped tablet. The tablet also comprised at least one band of polyolefin material which was fitted onto the tablet in such way that it located at midpoint. Swelling of tablet would enhance the gastric retention. The use of polyolefin band restricts their utility as it may not be biocompatible. Shell disclosed in U.S. Pat. No. 5,582,837 a dosage form which comprised multiple pellets. The pellets were prepared by mixing the hydrophilic soluble polymer like hydroxypropyl cellulose, the drug and other ingredients and compressing into pellets. A combination of pellets dispersed within a tablet or filled in a capsule to form a dosage form. The pellets were in the size of 3-9 mm and they exited immediately once the dosage form was placed in the aqueous medium. The pellets swelled upto 2 times in 1-3 hours and swelled upto 5 times in about 5 hours. The swollen particles released the drug by diffusion over an extended period of time. It was claimed that the swelled particles could not pass through the pylorus so that it would be retained in the stomach.

The release of sparingly soluble drugs by diffusion is dependent on the amount of fluid present in the stomach. In this case the disclosed composition in U.S. Pat. No. 5,582,837 may not be effective as it released the drug by diffusion. An alternative composition as disclosed by Shell et al. in U.S. Pat. No. 5,972,389 comprised an erodible polymer like polyethylene oxide wherein the drug releases occurred by erosion of the polymer. The preferred shapes of the said dosage forms to obtain the gastric retention were described by Merner et al. in U.S. Pat. No. 6,488,962. The gastroretentive tablet comprising hydroxylpropylmethyl cellulose did not swell significantly in the gastric fluid as compared to tablet comprising polyethylene oxide. However, polyethylene oxide eroded faster and an initial burst release of the drug was observed from the tablet. The amount of polyethylene oxide needed to achieve the desired level of swelling of the tablet was high and it is not acceptable in view of the polymer toxicity. In the gastroretentive composition disclosed by Gusler et al in U.S. Pat. No. 6,723,340 B2 a portion of polyethylene oxide was replaced by hydroxypropylmethyl cellulose to overcome this problem.

The prior art review shows several approaches that have been tried to provide a gastroretentive dosage forms that achieve the objective of releasing drug within the stomach; the disadvantages of such delivery systems were varied such as lack of mucoadhesion, the need of fluid to remain floating and the risk of gastrointestinal tract obstruction. Swellable gastroretentive dosage forms comprising pH independent polymers like hydroxypropylmethyl cellulose and polyethylene oxide which, are associated with low swelling and initial burst release of the drug respectively. It is also essential that such swellable dosage form attain the desired size within a short time, otherwise the dosage may pass through the pylorus and swell in the intestinal region which is undesirable. This application describes gastroretentive dosage form comprising the pH dependent graft copolymer. The dosage form floats and swells once it is placed in the medium which simulates acidic pH prevalent in the stomach, and maintains its integrity for the entire duration over which the drug is released from the dosage form.

OBJECT OF INVENTION

The main object of the present invention is to provide a gastroretentive, extended release composition that is retained in the stomach and releases the drug for an extended period of time.

The object of the present invention is to provide a gastroretentive, extended release composition which floats at acidic pH prevalent in the stomach.

Further object of the present invention is to provide a gastroretentive, extended release composition which swells and expands on floating.

Further object of the invention is to provide a gastroretentive, extended release composition formulated with the polymer which swells and then disintegrates/dissolves at acidic pH prevalent in the stomach.

Yet another object of the invention is to provide a gastroretentive, extended release composition which is easy to swallow.

SUMMARY OF THE INVENTION

Accordingly, the present invention relates to a gastroretentive, extended release composition for oral administration comprising:
  a. A graft copolymer which exhibits pH dependent behavior, represented by formula 1

Formula 1 wherein the said graft copolymer comprises:
    I. a backbone having the formula P $[A_{(x)} B_{(y)} C_{(z)}]$ comprising: a diol (A), a dicarboxylic acid or add anhydride (B) and a monomer containing pendent unsaturation (C) wherein (x)=41-45%, (y)=49-53% (z)=4-7% by mole; and
    II. a graft which is a polymer of the basic monomer (D) and 'w' is a weight percent of the total weight of said graft copolymer such that 'w' is 22-52%.
  b. a gellable polymer, (c) a therapeutically active agent (d) a gas generating system; and (e) pharmaceutically acceptable ingredients.

In an embodiment of the present invention, the backbone is an unsaturated polyester.

In another embodiment of the present invention, the diol is selected from the group consisting of aliphatic diols, cycloaliphatic diols and aromatic diols.

In another embodiment of the present invention the aliphatic diol is selected from the group consisting of 1,2-ethane diol, 1,3-propane diol, 1,2-propane diol, 2-methyl-1,3-propane diol, 1,4-butane diol, 1,3-butane diol, 1,2-butane diol, 1,5-pentane diol, 1,6-hexane diol, 1,7-heptane diol, 1,8-octane diol, 1,9-nonane diol, and 1,12-dodecane diol.

In another embodiment of the present invention, the cycloaliphatic diol used is 1,4-cyclohexanedimethanol.

In another embodiment of the present invention, the aromatic diol is bis(2-hydroxyethyl)terephthalate.

In another embodiment of the present invention, the dicarboxylic acid is selected from the group consisting of aliphatic and aromatic dicarboxylic acids.

In another embodiment of the present invention, the aliphatic dicarboxylic acid is selected from the group consisting of succinic acid, glutaric acid, adipic acid, pimelic acid, suberic acid, azelaic acid, sebacic acid, and dodecanedioic acid.

In another embodiment of the present invention, the acid anhydride is selected from the group consisting of succinic anhydride and phthalic anhydride.

In another embodiment of the present invention, the monomer containing pendent unsaturation is an epoxy monomer or a diol monomer.

In another embodiment of the present invention, the epoxy monomer containing pendent unsaturation is selected from the group consisting of glycidyl methacrylate and glycidyl acrylate.

In another embodiment of the present invention, the diol monomer containing pendent unsaturation is selected from the group consisting of trimethylolpropane monomethacrylate and trimethylolpropane monoacrylate.

In another embodiment of the present invention, the basic monomer is a tertiary amine.

In another embodiment of the present invention, the tertiary amine is a heterocyclic compound.

In another embodiment of the present invention, the heterocyclic compound is selected from the group consisting of 2-vinyl pyridine, 3-vinyl pyridine and 4-vinyl pyridine.

In another embodiment of the present invention, the heterocyclic compound is 4-vinylpyridine.

In another embodiment of the present invention, the pH dependent graft copolymer comprises 20-40% of the total weight of the formulation.

In another embodiment of the present invention, the gellable polymer is selected from the group consisting of cellulosic polymers, alginate polymers and polyalkene oxide.

In another embodiment of the present invention, the gellable polymer is selected from the group consisting of hydroxypropylmethyl cellulose, hydroxyethyl cellulose, xanthan gum, guar gum, sodium alginate and polyethylene oxide.

In another embodiment of the present invention, wherein the gellable polymer comprises 20-40% of the total weight of the formulation.

In another embodiment of the present invention the therapeutically active agent is selected from the group consisting of but not limited to antibiotic drugs, cardiovascular drugs and vitamins.

In another embodiment of the present invention, the antibiotic drug is selected from the group consisting of ciprofloxacin, ampicillin, ofloxacin, amoxicillin and cephalexin.

In another embodiment of the present invention, the cardiovascular drug is selected from the group consisting of verapamil, nifedepine, captopril, propranolol, atenolol and diltiazem.

In another embodiment of the present invention, vitamin is selected from the group consisting of thiamine hydrochloride, riboflavin 5'-phosphate sodium, pyridoxine hydrochloride and L-(+)-ascorbic acid.

In another embodiment of the present invention, the therapeutically active agent comprises 10-50% of the total weight of the formulation.

In another embodiment of the present invention, the gas generating system comprises a gas generating agent and a carboxyl compound.

In another embodiment of the present invention, the gas generating agent is selected from the group consisting of alkali carbonates and bicarbonates.

In another embodiment of the present invention the gas generating agent is selected from the group consisting of sodium carbonate, calcium carbonate, sodium bicarbonate and potassium bicarbonate.

In another embodiment of the present invention, the carboxyl compound is selected from the group consisting of malic acid, fumaric acid, tartaric acid, citric acid and ascorbic acid.

In another embodiment of the present invention, the gas generating system comprises 12-18% of the total weight of the formulation In another embodiment of the present invention, the gastroretentive, extended release composition is produced in pharmaceutical solid dosage form.

In another embodiment of the present invention, the solid dosage form floats in acidic pH In another embodiment of the present invention, the solid dosage form swells and expands on floating.

DETAILED DESCRIPTION OF THE INVENTION

Figure 1:
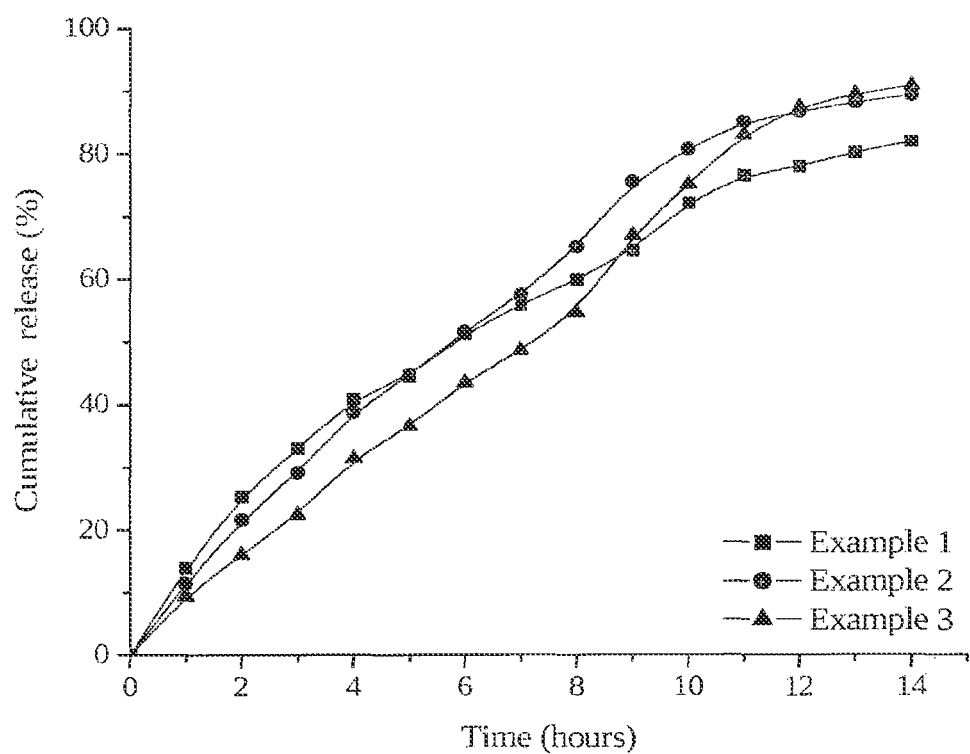
FIG. 1. Release profile of gastroretentive, extended release tablet comprising ciprofloxacin hydrochloride.
Figure 2:
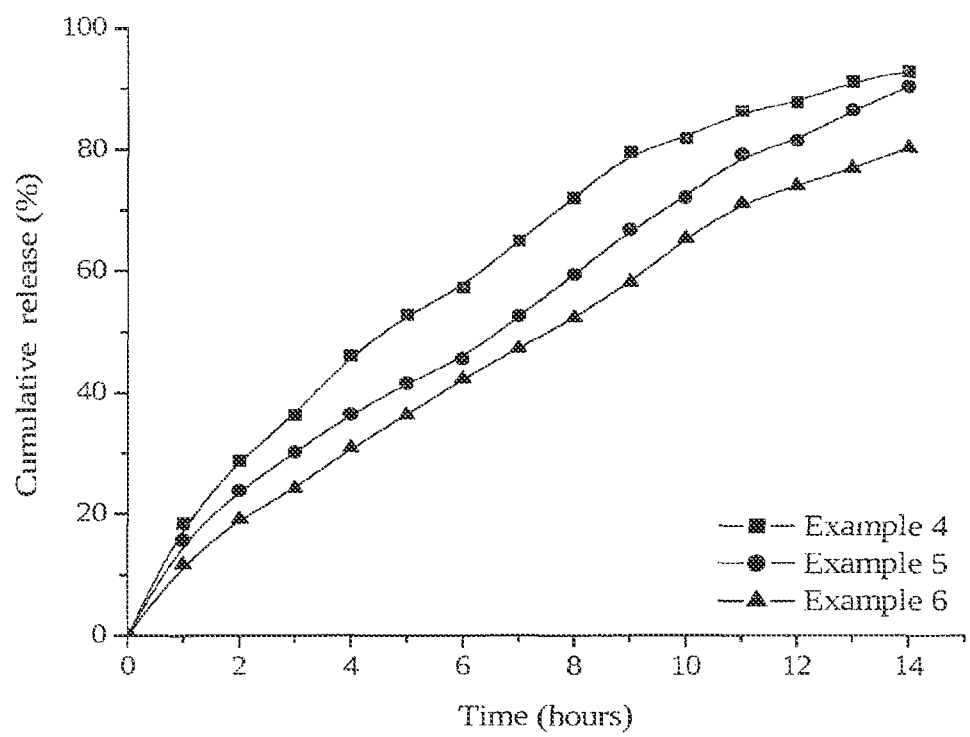
FIG. 2. Release profile gastroretentive, extended release tablet comprising cephalexin monohydrate.
Figure 3:
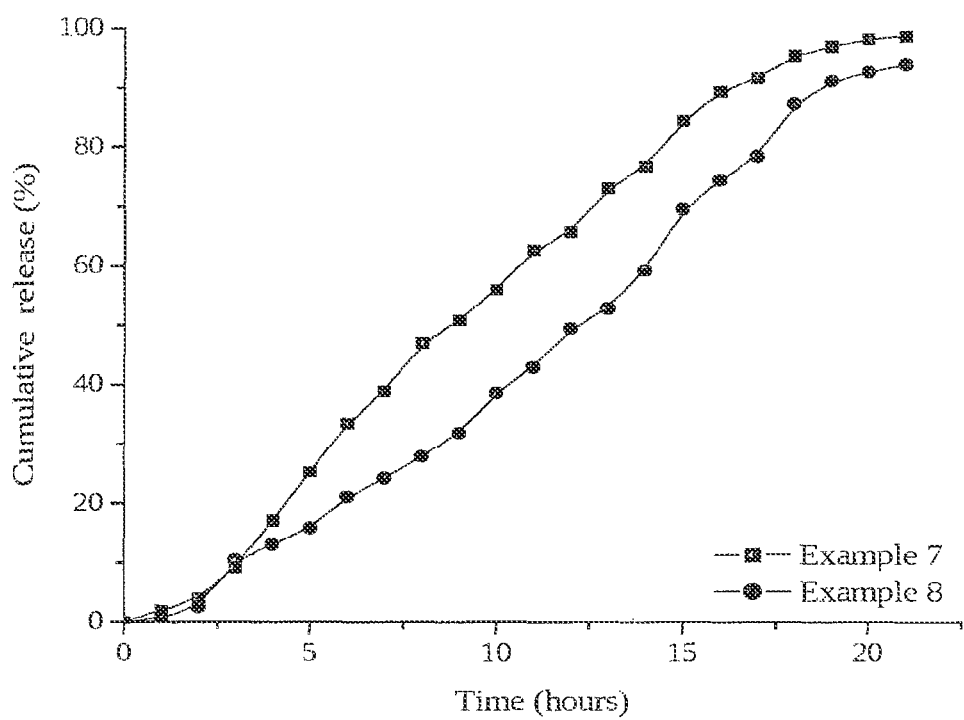
FIG. 3. Release profile gastroretentive, extended release tablet comprising riboflavin 5'-phosphate sodium.
Figure 4:
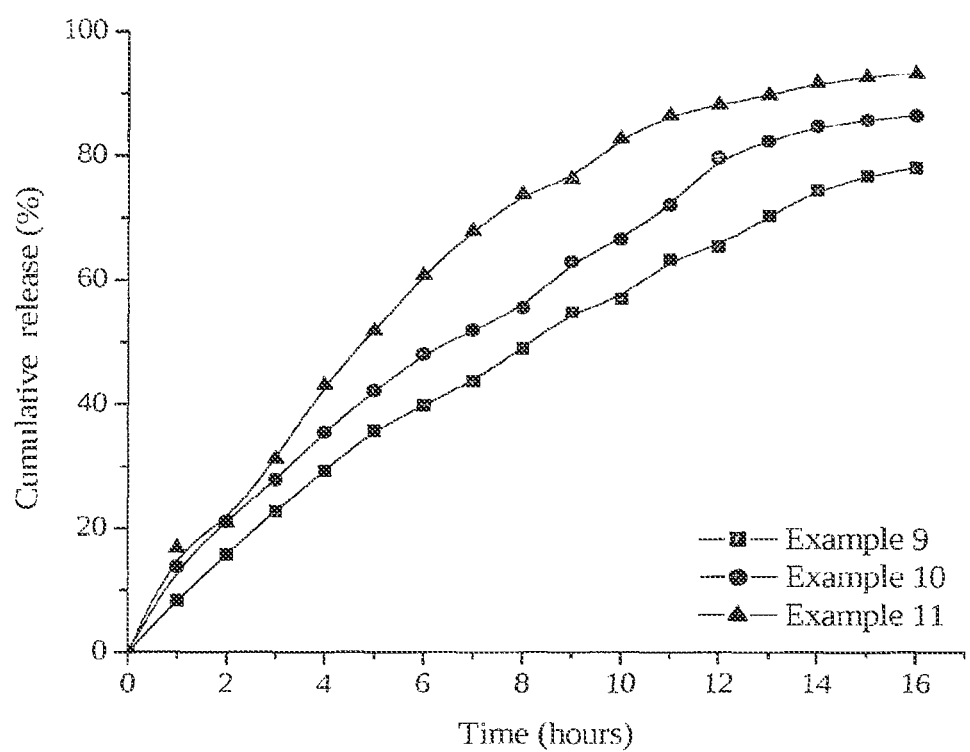
FIG. 4. Release profile gastroretentive, extended release tablet comprising diltiazem hydrochloride.
Figure 5:
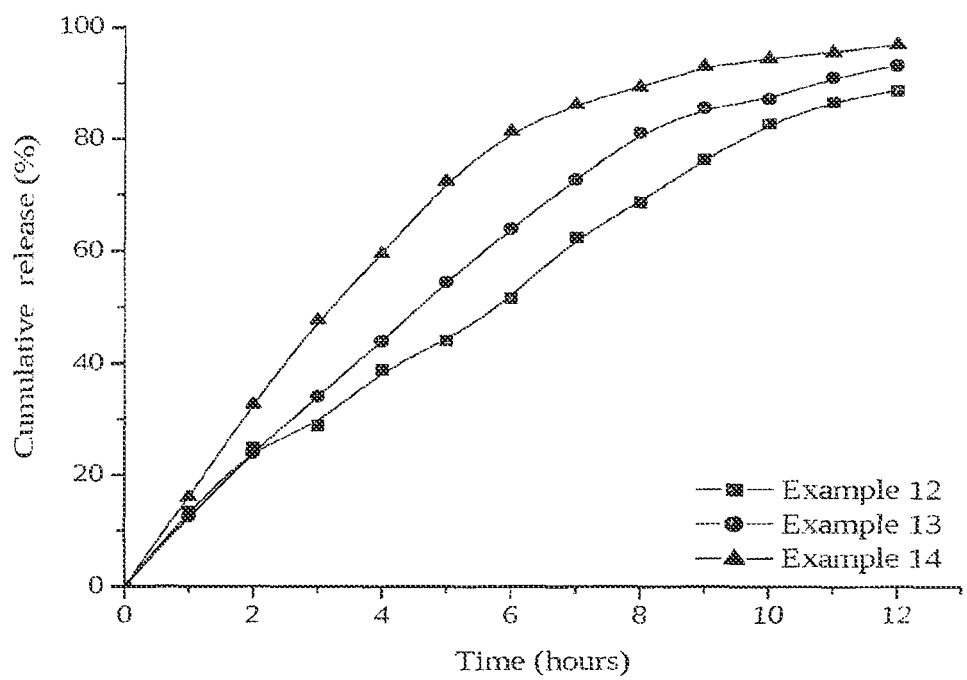
FIG. 5. Release profile gastroretentive, extended release tablet comprising ciprofloxacin hydrochloride.
Figure 6:
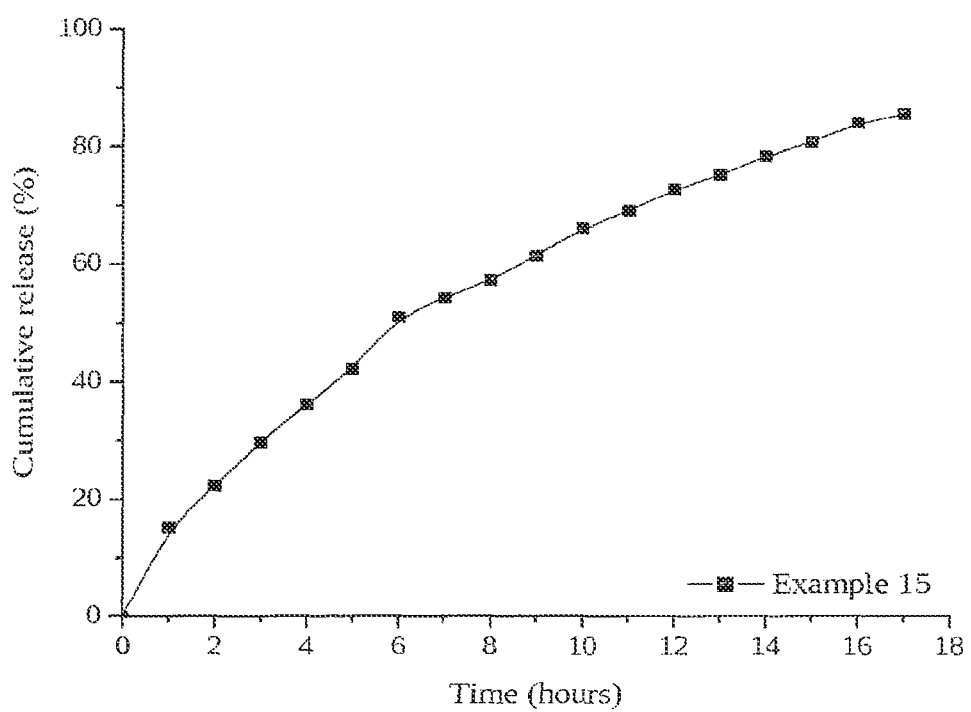
FIG. 6. Release profile of gastroretentive, extended release tablet comprising ofloxacin.

The present invention discloses a gastroretentive, extended release composition which comprises;
(a) A graft copolymer which exhibits pH dependent behavior, represented by formula 1

Formula 1 wherein the said graft copolymer comprises:
I. a backbone having the formula P $[A_{(x)} B_{(y)} C_{(z)}]$ comprising: a dial (A), a dicarboxylic acid or acid anhydride (B) and a monomer containing pendent unsaturation (C) wherein (x)=41-45%, (y)=49-53% (z)=4-7% by mole; and
II. a graft which is a polymer of the basic monomer (D) and 'w' is a weight percent of the total weight of said graft copolymer such that 'w' is 22-52%.

The backbone of pH dependent graft copolymer is polyester. The components for the preparation of said polyester selected are as follows.

The diol (A) is selected from the group comprising aliphatic diols and cycloaliphatic dials. The aliphatic diols are selected from 1,2-ethane diol, 1,3-propane diol, 1,2-propane diol, 2-methyl-1,3-propane diol, 1,4-butane diol, 1,3-butane diol, 1,2-butane diol, 1,5-pentane diol, 1,6-hexane diol, 1,7-heptane diol, 1,8-octane diol, 1,9-nonane diol, 1,12-dodecane dial. The cycloaliphatic dial is 1,4-cyclohexanedimethanol.

The dicarboxylic acids or acid anhydrides (B) are selected from aliphatic dicarboxylic acid such as succinic acid, glutaric acid, adipic acid, pimelic acid, suberic acid, azelaic acid, sebacic acid dodecanedioic acid and succinic anhydride. The aromatic anhydride is phthalic anhydride. In one aspect of the invention, B is an aromatic dicarboxylic acid.

The monomer containing pendent unsaturation (C) is selected from an epoxy compound such as glycidyl methacrylate, glycidyl acrylate and such like. In another aspect of the invention, C is a diol compound selected from trimethylolpropane monomethacrylate, trimethylolpropane mono acrylate and such like.

The basic monomer (D) for the preparation of pH dependent graft copolymer is selected from 2-vinylpyridine, 3-vinylpyridine and 4-vinylpyridine.

The therapeutically active agent incorporated in the gastroretentive, extended release composition is selected from but not limited to the group comprising antibiotic drugs, cardiovascular drugs and vitamins.

The gellable polymer incorporated in the gastroretentive, extended release composition is selected from the group comprising cellulosic polymers, alginate polymers and polyalkene oxide.

The gas generating system incorporated in the gastroretentive, extended release composition comprises a gas generating agent and a carboxyl compound. The gas generating agent is alkali carbonates and bicarbonates such as sodium carbonate, calcium carbonate, sodium bicarbonate, potassium bicarbonate and such like. The carboxyl compound is selected from succinic acid, malic acid, maleic acid, fumaric acid, tartaric acid, citric acid and ascorbic acid.

The gastroretentive, extended release composition further comprises various pharmaceutically acceptable ingredients such as lubricants, fillers, binders, flavours, colours, anti adherents, glidants, other aides and such like.

The gastroretentive, extended release composition is prepared in pharmaceutical solid dosage form such as tablets, pills and capsules. In one of the embodiment the compositions are in the form of tablets. Such a tablet comprises a therapeutically active agent in the range of 10-50%, at least one pH dependent graft copolymer in the range of 20-40%, at lease one gellable polymer in the range of 20-40%, a gas generating system in the range of 12-18% of the total weight of the formulation.

The gastroretentive, extended release tablet was prepared by dry granulation method. A therapeutically active agent, a pH dependent graft copolymer, a gellable polymer and a gas generating system were dry granulated. To this a pharmaceutically acceptable lubricant was added and mixed thoroughly. The granular mixture was compressed into the tablet in the size of 13 mm in diameter. In-vitro evaluation of gastroretentive, extended release composition was carried out by USP dissolution apparatus using paddle method. The solid dosage forms as exemplified herein displayed floating behavior in acidic pH and swelled and expanded on floating.

The following examples are presented in order to further illustrate the invention. These examples should not be construed in any manner to limit the invention.

In the examples the diol, dibasic acid, unsaturated monomer and acidic monomer are described by the following abbreviations.

1,4 BD-1,4 Butane diol, 1,12 DD-1,12 Dodecane diol, 1,4 CD-1,4 Cyclohexane dimethanol, SA-Succinic acid, SEB-Sebacic acid, AA-Adipic acid, DDA-Dodecanedioic acid, GMA-Glycidyl methacrylate, TMPMA-Trimethylolpropane monomethacrylate, 4VP-4 Vinylpyridine.

The synthesis of pH sensitive graft copolymers based on the above monomers is described in our copending Indian patent application 0530DEL2010, the content of which is incorporated and included as if set forth fully herein.

Comparative Example 1

This example describes the preparation and the dissolution profile of diltiazem hydrochloride tablet comprising the pH dependent copolymer of methylmethacrylate, dimethylaminoethyl methacrylate and butylmethacrylate.

(a) Preparation of Diltiazem Hydrochloride Tablet

The drug diltiazem hydrochloride, the pH dependent copolymer, the gellable polymer hydroxypropylmethyl cellulose (K4M), the gas generating system comprising sodium bicarbonate and citric acid were dry granulated. To this the lubricant magnesium stearate was added and mixed thoroughly and then compressed into tablet 13 mm in diameter. The composition of the tablet is given in Table 1.

TABLE 1

Composition of diltiazem hydrochloride tablet

| Tablet Composition | Weight (mg) |
| --- | --- |
| Diltiazem Hydrochloride | 125.00 |
| pH dependent copolymer | 250.00 |
| Gellable polymer | 50.00 |
| Sodium bicarbonate | 30.00 |
| Citric acid | 30.00 |
| Magnesium stearate | 15.00 |
| Total | 500.00 |

(b) Dissolution of Diltiazem Hydrochloride

The dissolution of diltiazem hydrochloride was monitored using a USP dissolution apparatus and paddle method at 50 rpm. The dissolution medium was 0.1 N HCL and the temperature was maintained at 37±0.5° C. The tablet did not swell but dissolved and released the drug within 3 hours. Since this composition did not swell and released the drug within 3 hours it does not serve as a gastroretentive device.

Comparative Example 2

This example describes the preparation and the dissolution profile of diltiazem hydrochloride comprising the pH dependent copolymer of methylmethacrylate, dimethylaminoethyl methacrylate and butylmethacrylate.

(a) Preparation of Diltiazem Hydrochloride Tablet

The drug diltiazem hydrochloride, the pH dependent copolymer, the gellable polymer hydroxypropylmethyl cellulose (K4M), the gas generating system comprising sodium bicarbonate and citric acid were dry granulated. To this the lubricant magnesium stearate was added and mixed thoroughly and then compressed into tablet 13 mm in diameter. The composition of the tablet is given in Table 2.

TABLE 2

Composition of diltiazem hydrochloride tablet

| Tablet Composition | Weight (mg) |
| --- | --- |
| Diltiazem Hydrochloride | 125.00 |
| pH dependent copolymer | 200.00 |
| Gellable polymer | 100.00 |
| Sodium bicarbonate | 30.00 |
| Citric acid | 30.00 |
| Magnesium stearate | 15.00 |
| Total | 500.00 |

(b) Dissolution of Diltiazem Hydrochloride

The dissolution of diltiazem hydrochloride was monitored using a USP dissolution apparatus and paddle method at 50 rpm. The dissolution medium was 0.1 N HCl and the temperature was maintained at 37±0.5° C. Although the drug was released over a period of 6 hours, the tablet did not swell. The composition therefore is not suitable as a gastroretentive delivery device.

Comparative Example 3

This example describes the preparation and the dissolution profile of diltiazem hydrochloride tablet comprising the pH dependent Copolymer of methylmethacrylate, dimethylaminoethyl methacrylate and butylmethacrylate.

(a) Preparation of Diltiazem Hydrochloride Tablet

The drug diltiazem hydrochloride, the pH dependent copolymer, the gellable polymer hydroxypropylmethyl cellulose (K4M), the gas generating system comprising sodium bicarbonate and citric acid were dry granulated. To this the lubricant magnesium stearate was added and mixed thoroughly and then compressed into tablet 13 mm in diameter. The composition of the tablet is given in Table 3.

TABLE 3

Composition of diltiazem hydrochloride tablet

| Tablet Composition | Weight (mg) |
| --- | --- |
| Diltiazem Hydrochloride | 125.00 |
| pH dependent copolymer | 150.00 |
| Gellable polymer | 150.00 |
| Sodium bicarbonate | 30.00 |
| Citric acid | 30.00 |
| Magnesium stearate | 15.00 |
| Total | 500.00 |

(b) Dissolution of Diltiazem Hydrochloride

The dissolution of diltiazem hydrochloride was monitored using a USP dissolution apparatus and paddle method at 50 rpm. The dissolution medium was 0.1 N HCL and the temperature was maintained at 37±0.5° C. Although the drug was released over a period of 7 hours, the tablet did not swell. The composition therefore is not suitable as a gastroretentive delivery device.

Example 1

This example describes the preparation and the dissolution profile of ciprofloxacin hydrochloride gastroretentive tablet comprising the pH dependent graft copolymer

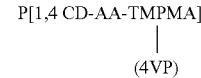

where in the 4VP content is 31%.

(a) Preparation of Ciprofloxacin Hydrochloride Gastrotentive Tablet

The drug ciprofloxacin hydrochloride, the pH dependent graft copolymer, the gellable polymer hydroxypropylmethyl cellulose (K4M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 4.

TABLE 4

Composition of ciprofloxacin hydrochloride gastroretentive tablet

| Tablet Composition | Weight (mg) |
|---|---|
| Ciprofloxacin Hydrochloride | 125.00 |
| pH dependent graft copolymer | 200.00 |
| Gellable polymer | 100.00 |
| Sodium bicarbonate | 30.00 |
| Citric acid | 30.00 |
| Magnesium stearate | 15.00 |
| Total | 500.00 |

(b) Dissolution of Ciprofloxacin Hydrochloride

The dissolution of ciprofloxacin hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 5.

TABLE 5

Dissolution of ciprofloxacin hydrochloride

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 13.86 | 25.35 | 33.02 | 40.82 | 44.54 | 51.22 | 55.86 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 59.94 | 64.58 | 72.19 | 76.46 | 77.95 | 80.18 | 81.89 |

Example 2

This example describes the preparation and the dissolution profile of ciprofloxacin hydrochloride gastroretentive tablet comprising the pH dependent graft copolymer

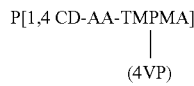

where in the 4VP content is 38%.

(a) Preparation of Ciprofloxacin Hydrochloride Gastroretentive Tablet

The drug ciprofloxacin hydrochloride, the pH dependent graft copolymer, the gellable polymer hydroxypropylmethyl cellulose (K4M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 6.

TABLE 6

Composition of ciprofloxacin hydrochloride gastroretentive tablet

| Tablet Composition | Weight (mg) |
|---|---|
| Ciprofloxacin Hydrochloride | 125.00 |
| pH dependent graft copolymer | 150.00 |
| Gellable polymer | 150.00 |
| Sodium bicarbonate | 30.00 |
| Citric acid | 30.00 |
| Magnesium stearate | 15.00 |
| Total | 500.00 |

(b) Dissolution of Ciprofloxacin Hydrochloride

The dissolution of ciprofloxacin hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 7.

TABLE 7

Dissolution of ciprofloxacin hydrochloride

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 11.40 | 21.55 | 29.13 | 38.78 | 44.72 | 51.59 | 57.53 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 65.13 | 75.53 | 80.73 | 85.00 | 86.67 | 88.16 | 89.27 |

Example 3

This example describes the preparation and the dissolution profile of ciprofloxacin hydrochloride gastroretentive tablet comprising the pH dependent graft copolymer

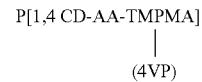

where in the 4VP content is 38%.

(a) Preparation of Ciprofloxacin Hydrochloride Gastroretentive Tablet

The drug ciprofloxacin hydrochloride, the pH dependent graft copolymer, the gellable polymer hydroxypropylmethyl cellulose (K4M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 8.

TABLE 8

Composition of ciprofloxacin hydrochloride gastroretentive tablet

| Tablet Composition | Weight (mg) |
|---|---|
| Ciprofloxacin Hydrochloride | 125.00 |
| pH dependent graft copolymer | 100.00 |
| Gellable polymer | 200.00 |
| Sodium bicarbonate | 30.00 |
| Citric acid | 30.00 |
| Magnesium stearate | 15.00 |
| Total | 500.00 |

(b) Dissolution of Ciprofloxacin Hydrochloride

The dissolution of ciprofloxacin hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 9.

TABLE 9

Dissolution of ciprofloxacin hydrochloride

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 9.42 | 16.13 | 22.45 | 31.35 | 36.55 | 43.60 | 48.62 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 54.74 | 66.99 | 75.16 | 82.95 | 87.41 | 89.46 | 90.76 |

Example 4

This example describes the preparation and the dissolution profile of cephalexin monohydrate gastroretentive tablet comprising the pH dependent graft copolymer

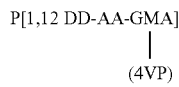

where in the 4VP content is 27%.

(a) Preparation of Cephalexin Monohydrate Gastroretentive Tablet

The drug cephalexin monohydrate, the pH dependent graft copolymer, the gellable polymer hydroxypropylmethyl cellulose (K100M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 10.

TABLE 10

Composition of cephalexin monohydrate gastroretentive tablet

| Tablet Composition | Weight (mg) |
|---|---|
| Cephalexin monohydrate | 150.00 |
| pH dependent graft copolymer | 125.00 |
| Gellable polymer | 150.00 |
| Sodium bicarbonate | 35.00 |
| Citric acid | 35.00 |
| Magnesium stearate | 5.00 |
| Total | 500.00 |

(b) Dissolution of Cephalexin Monohydrate

The dissolution of cephalexin monohydrate was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 11.

TABLE 11

Dissolution of cephalexin monohydrate

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 18.50 | 28.88 | 36.34 | 46.16 | 52.93 | 57.36 | 65.10 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 72.15 | 79.61 | 81.97 | 86.39 | 87.78 | 91.23 | 92.89 |

Example 5

This example describes the preparation and the dissolution profile of cephalexin monohydrate gastroretentive tablet comprising the pH dependent graft copolymer

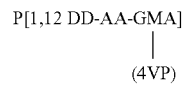

where in the 4VP content is 36%.

(a) Preparation of Cephalexin Monohydrate Gastroretentive Tablet

The drug cephalexin monohydrate, the pH dependent graft copolymer, the gellable polymer hydroxypropylmethyl cellulose (K100M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 12.

TABLE 12

Composition of cephalexin monohydrate gastroretentive tablet

| Tablet Composition | Weight (mg) |
|---|---|
| Cephalexin monohydrate | 150.00 |
| pH dependent graft copolymer | 125.00 |
| Gellable polymer | 150.00 |
| Sodium bicarbonate | 35.00 |
| Citric acid | 35.00 |
| Magnesium stearate | 5.00 |
| Total | 500.00 |

(b) Dissolution of Cephalexin Monohydrate

The dissolution of cephalexin monohydrate was monitored using a USP dissolution apparatus and paddle method at 50 rpm. The dissolution medium was 0.1 N HCL and the temperature was maintained at 37±0.5° C., A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 13.

TABLE 13

Dissolution of cephalexin monohydrate

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 15.74 | 23.90 | 30.26 | 36.48 | 41.60 | 45.61 | 52.66 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 59.43 | 66.90 | 72.15 | 79.20 | 81.56 | 86.53 | 90.40 |

Example 6

This example describes the preparation and the dissolution profile of cephalexin monohydrate gastroretentive tablet comprising the pH dependent graft copolymer

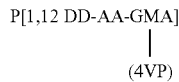

where in the 4VP content is 45%.

(a) Preparation of Cephalexin Monohydrate Gastroretentive Tablet

The drug cephalexin monohydrate, the pH dependent graft copolymer, the gellable polymer hydroxypropylmethyl cellulose (K100M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 14.

TABLE 14

Composition of cephalexin monohydrate gastroretentive tablet

| Tablet Composition | Weight (mg) |
|---|---|
| Cephalexin monohydrate | 150.00 |
| pH dependent graft copolymer | 125.00 |
| Gellable polymer | 150.00 |
| Sodium bicarbonate | 35.00 |
| Citric acid | 35.00 |
| Magnesium stearate | 5.00 |
| Total | 500.00 |

(b) Dissolution of Cephalexin Monohydrate

The dissolution of cephalexin monohydrate was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 15.

TABLE 15

Dissolution of cephalexin monohydrate

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 11.73 | 19.20 | 24.18 | 30.95 | 36.35 | 42.29 | 47.27 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 52.38 | 58.19 | 65.38 | 71.18 | 74.09 | 76.99 | 80.31 |

Example 7

This example describes the preparation and the dissolution profile of riboflavin 5'-phosphate sodium gastroretentive tablet comprising the pH dependent graft copolymer

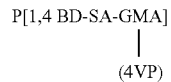

where in the 4VP content is 49%.

(a) Preparation of Riboflavin 5'-Phosphate Sodium Gastroretentive Tablet

The drug riboflavin 5'-phosphate sodium, the pH dependent graft copolymer, the gellable polymer polyethylene oxide (WSX 303), the as generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 16.

TABLE 16

Composition of riboflavin 5'-phosphate sodium gastroretentive tablet

| Tablet Composition | Weight (mg) |
|---|---|
| Riboflavin 5'-phosphate sodium | 50.00 |
| pH dependent graft copolymer | 150.00 |
| Gellable polymer | 200.00 |
| Sodium bicarbonate | 45.00 |
| Citric acid | 45.00 |
| Magnesium stearate | 10.00 |
| Total | 500.00 |

(b) Dissolution of Riboflavin 5'-Phosphate Sodium

The dissolution of riboflavin 5'-phosphate sodium was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 17.

TABLE 17

Dissolution of riboflavin 5'-phosphate sodium

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 1.99 | 3.99 | 9.23 | 17.22 | 25.47 | 33.46 | 38.96 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 46.95 | 50.95 | 55.95 | 62.69 | 65.69 | 73.18 | 76.68 |

| | Time (hours) | | | | | | |
|---|---|---|---|---|---|---|---|
| | 15.0 | 16.0 | 17.0 | 18.0 | 19.0 | 20.0 | 21.0 |
| % Dissolved (Cumulative) | 84.42 | 89.42 | 91.67 | 95.42 | 96.92 | 98.17 | 98.67 |

Example 8

This example describes the preparation and the dissolution profile of riboflavin 5'-phosphate sodium gastroretentive tablet comprising the pH dependent graft copolymer

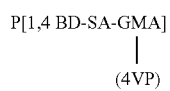

where in the 4VP content is 49%.

(a) Preparation of Riboflavin 5'-Phosphate Sodium Gastroretentive Tablet

The drug riboflavin 5'-phosphate sodium, the pH dependent graft copolymer, the gellable polymer polyethylene oxide (WSX 303), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 18.

TABLE 18

Composition of riboflavin 5'-phosphate sodium gastroretentive tablet

| Tablet Composition | Weight (mg) |
|---|---|
| Riboflavin 5'-phosphate sodium | 75.00 |
| pH dependent graft copolymer | 125.00 |
| Gellable polymer | 200.00 |
| Sodium bicarbonate | 45.00 |
| Citric acid | 45.00 |
| Magnesium stearate | 10.00 |
| Total | 500.00 |

(b) Dissolution of Riboflavin 5'-Phosphate Sodium

The dissolution of riboflavin 5'-phosphate sodium was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained, its integrity for the entire duration over which the drug is released from the dosage form. The cumulative percent dissolution of the drug is summarized in the Table 19.

TABLE 19

Dissolution of riboflavin 5'-phosphate sodium

| | Time (hours) | | | | | | |
|---|---|---|---|---|---|---|---|
| | 1.0 | 2.0 | 3.0 | 4.0 | 5.0 | 6.0 | 7.0 |
| % Dissolved (Cumulative) | 0.66 | 2.49 | 10.48 | 13.15 | 15.81 | 21.14 | 24.31 |

| | Time (hours) | | | | | | |
|---|---|---|---|---|---|---|---|
| | 8.0 | 9.0 | 10.0 | 11.0 | 12.0 | 13.0 | 14.0 |
| % Dissolved (Cumulative) | 27.97 | 31.80 | 38.63 | 42.96 | 49.45 | 52.79 | 59.28 |

| | Time (hours) | | | | | | |
|---|---|---|---|---|---|---|---|
| | 15.0 | 16.0 | 17.0 | 18.0 | 19.0 | 20.0 | 21.0 |
| % Dissolved (Cumulative) | 69.60 | 74.43 | 78.43 | 87.25 | 91.09 | 92.59 | 93.92 |

Example 9

This example describes the preparation and the dissolution profile of diltiazem hydrochloride gastroretentive tablet comprising the pH dependent graft copolymer

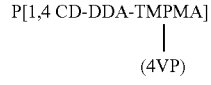

where in the 4VP content is 30%.

(a) Preparation of Diltiazem Hydrochloride Gastroretentive Tablet

The drug diltiazem hydrochloride, the pH dependent graft copolymer, the gellable polymer hydroxypropylmethyl cellulose (K15M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 20.

TABLE 20

Composition of diltiazem hydrochloride gastroretentive tablet

| Tablet Composition | Weight (mg) |
|---|---|
| Diltiazem hydrochloride | 200.00 |
| pH dependent graft copolymer | 100.00 |
| Gellable polymer | 125.00 |
| Sodium bicarbonate | 35.00 |
| Citric acid | 35.00 |
| Magnesium stearate | 5.00 |
| Total | 500.00 |

(b) Dissolution of Diltiazem Hydrochloride

The dissolution of diltiazem hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 21.

TABLE 21

Dissolution of diltiazem hydrochloride

| | Time (hours) | | | | | | | |
|---|---|---|---|---|---|---|---|---|
| | 1.0 | 2.0 | 3.0 | 4.0 | 5.0 | 6.0 | 7.0 | 8.0 |
| % Dissolved (Cumulative) | 8.40 | 15.80 | 22.76 | 29.28 | 35.81 | 39.73 | 43.79 | 49.01 |

| | Time (hours) | | | | | | | |
|---|---|---|---|---|---|---|---|---|
| | 9.0 | 10.0 | 11.0 | 12.0 | 13.0 | 14.0 | 15.0 | 16.0 |
| % Dissolved (Cumulative) | 54.81 | 56.99 | 63.37 | 65.40 | 70.33 | 74.39 | 76.71 | 78.02 |

Example 10

This example describes the preparation and the dissolution profile of diltiazem hydrochloride gastroretentive tablet comprising the pH dependent graft copolymer

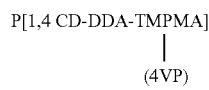

where in the 4VP content is 38%.

(a) Preparation of Diltiazem Hydrochloride Gastroretentive Tablet

The drug diltiazem hydrochloride, the pH dependent graft copolymer, the gellable polymer hydroxypropylmethyl cellulose (K15M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 22.

TABLE 22

Composition of diltiazem hydrochloride gastroretentive tablet

| Tablet Composition | Weight (mg) |
|---|---|
| Diltiazem hydrochloride | 200.00 |
| pH dependent graft copolymer | 100.00 |
| Gellable polymer | 125.00 |
| Sodium bicarbonate | 35.00 |
| Citric acid | 35.00 |
| Magnesium stearate | 5.00 |
| Total | 500.00 |

(b) Dissolution of Diltiazem Hydrochloride

The dissolution of diltiazem hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 23.

TABLE 23

Dissolution of diltiazem hydrochloride

| | Time (hours) | | | | | | | |
|---|---|---|---|---|---|---|---|---|
| | 1.0 | 2.0 | 3.0 | 4.0 | 5.0 | 6.0 | 7.0 | 8.0 |
| % Dissolved (Cumulative) | 13.76 | 21.02 | 27.83 | 35.37 | 42.19 | 47.99 | 51.91 | 55.54 |

| | Time (hours) | | | | | | | |
|---|---|---|---|---|---|---|---|---|
| | 9.0 | 10.0 | 11.0 | 12.0 | 13.0 | 14.0 | 15.0 | 16.0 |
| % Dissolved (Cumulative) | 62.93 | 66.56 | 72.07 | 79.61 | 82.37 | 84.69 | 85.71 | 86.43 |

Example 11

This example describes the preparation and the dissolution profile of diltiazem hydrochloride gastroretentive tablet comprising the pH dependent graft copolymer

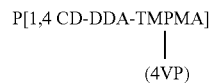

where in the 4VP content is 50%.

(a) Preparation of Diltiazem Hydrochloride Gastroretentive Tablet

The drug diltiazem hydrochloride, the pH dependent graft copolymer, the gellable polymer hydroxypropylmethyl cellulose (K15M), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 24.

TABLE 24

Composition of diltiazem hydrochloride gastroretentive tablet

| Tablet Composition | Weight (mg) |
|---|---|
| Diltiazem hydrochloride | 200.00 |
| pH dependent graft copolymer | 100.00 |
| Gellable polymer | 125.00 |
| Sodium bicarbonate | 35.00 |
| Citric acid | 35.00 |
| Magnesium stearate | 5.00 |
| Total | 500.00 |

(b) Dissolution of Diltiazem Hydrochloride

The dissolution of diltiazem hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 25.

TABLE 25

Dissolution of diltiazem hydrochloride

| | Time (hours) | | | | | | | |
|---|---|---|---|---|---|---|---|---|
| | 1.0 | 2.0 | 3.0 | 4.0 | 5.0 | 6.0 | 7.0 | 8.0 |
| % Dissolved (Cumulative) | 16.80 | 20.87 | 31.17 | 43.06 | 51.91 | 60.75 | 67.86 | 73.81 |

| | Time (hours) | | | | | | | |
|---|---|---|---|---|---|---|---|---|
| | 9.0 | 10.0 | 11.0 | 12.0 | 13.0 | 14.0 | 15.0 | 16.0 |
| % Dissolved (Cumulative) | 76.28 | 82.80 | 86.57 | 88.17 | 89.77 | 91.65 | 92.67 | 93.25 |

TABLE 26

Composition of ciprofloxacin hydrochloride gastroretentive tablet

| Tablet Composition | Weight (mg) |
|---|---|
| Ciprofloxacin Hydrochloride | 50.00 |
| pH dependent graft copolymer | 175.00 |
| Gellable polymer | 175.00 |
| Sodium bicarbonate | 45.00 |
| Citric acid | 45.00 |
| Magnesium stearate | 10.00 |
| Total | 500.00 |

(b) Dissolution of Ciprofloxacin Hydrochloride

The dissolution of ciprofloxacin hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 27.

TABLE 27

Dissolution of ciprofloxacin hydrochloride

| | Time (hours) | | | | | |
|---|---|---|---|---|---|---|
| | 1.0 | 2.0 | 3.0 | 4.0 | 5.0 | 6.0 |
| % Dissolved (Cumulative) | 13.40 | 24.83 | 28.83 | 38.82 | 43.96 | 51.67 |

| | Time (hours) | | | | | |
|---|---|---|---|---|---|---|
| | 7.0 | 8.0 | 9.0 | 10.0 | 11.0 | 12.0 |
| % Dissolved (Cumulative) | 62.52 | 68.81 | 76.51 | 82.80 | 86.80 | 88.80 |

Example 12

This example describes the preparation and the dissolution profile of ciprofloxacin hydrochloride gastroretentive tablet comprising the pH dependent graft copolymer

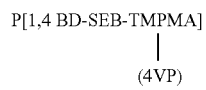

where in the 4VP content is 31%.

(a) Preparation of Ciprofloxacin Hydrochloride Gastroretentive Tablet

The drug ciprofloxacin hydrochloride, the pH dependent graft copolymer, the gellable polymer polyethylene oxide (WSX 303), the as generating system comprising sodium bicarbonate and citric add were dry granulated. To this the lubricant magnesium stearate was added and mixed thoroughly and then compressed into tablet 13 mm in diameter. The composition of the gastroretentive tablet is given in Table 26.

Example 13

This example describes the preparation and the dissolution profile of ciprofloxacin hydrochloride gastroretentive tablet comprising the pH dependent graft copolymer

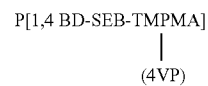

where in the 4VP content is 31%.

(a) Preparation of Ciprofloxacin Hydrochloride Gastroretentive Tablet

The drug ciprofloxacin hydrochloride, the pH dependent graft copolymer, the gellable polymer polyethylene oxide (WSX 303), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 28.

TABLE 28

Composition of ciprofloxacin hydrochloride gastroretentive tablet

| Tablet Composition | Weight (mg) |
|---|---|
| Ciprofloxacin Hydrochloride | 100.00 |
| pH dependent graft copolymer | 150.00 |
| Gellable polymer | 150.00 |
| Sodium bicarbonate | 45.00 |
| Citric acid | 45.00 |
| Magnesium stearate | 10.00 |
| Total | 500.00 |

(b) Dissolution of Ciprofloxacin Hydrochloride

The dissolution of ciprofloxacin hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 29.

TABLE 29

Dissolution of ciprofloxacin hydrochloride

| | Time (hours) | | | | | |
|---|---|---|---|---|---|---|
| | 1.0 | 2.0 | 3.0 | 4.0 | 5.0 | 6.0 |
| % Dissolved (Cumulative) | 12.51 | 23.92 | 34.04 | 43.91 | 54.51 | 64.07 |
| | Time (hours) | | | | | |
| | 7.0 | 8.0 | 9.0 | 10.0 | 11.0 | 12.0 |
| % Dissolved (Cumulative) | 72.83 | 81.26 | 85.68 | 87.21 | 91.06 | 93.23 |

Example 14

This example describes the preparation and the dissolution profile of ciprofloxacin hydrochloride gastroretentive tablet comprising the pH dependent graft copolymer

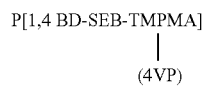

where in the 4VP content is 31%.

(a) Preparation of Ciprofloxacin Hydrochloride Gastroretentive Tablet

The drug ciprofloxacin hydrochloride, the pH dependent graft copolymer, the gellable polymer polyethylene oxide (WSX 303), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 30.

TABLE 30

Composition of ciprofloxacin hydrochloride gastroretentive tablet

| Tablet Composition | Weight (mg) |
|---|---|
| Ciprofloxacin Hydrochloride | 150.00 |
| pH dependent graft copolymer | 125.00 |
| Gellable polymer | 125.00 |
| Sodium bicarbonate | 45.00 |
| Citric acid | 45.00 |
| Magnesium stearate | 10.00 |
| Total | 500.00 |

(b) Dissolution of Ciprofloxacin Hydrochloride

The dissolution of ciprofloxacin hydrochloride was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 31.

TABLE 31

Dissolution of ciprofloxacin hydrochloride

| | Time (hours) | | | | | |
|---|---|---|---|---|---|---|
| | 1.0 | 2.0 | 3.0 | 4.0 | 5.0 | 6.0 |
| % Dissolved (Cumulative) | 16.06 | 32.61 | 47.62 | 59.53 | 72.52 | 81.50 |
| | Time (hours) | | | | | |
| | 7.0 | 8.0 | 9.0 | 10.0 | 11.0 | 12.0 |
| % Dissolved (Cumulative) | 86.30 | 89.39 | 93.10 | 94.50 | 95.58 | 96.97 |

Example 15

This example describes the preparation and the dissolution profile of ofloxacin gastroretentive tablet comprising the pH dependent graft copolymer

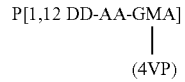

where in the 4VP content is 36%.

(a) Preparation of Ofloxacin Gastroretentive Tablet

The drug ofloxacin, the pH dependent graft copolymer, the gellable polymer polyethylene oxide (WSX 303), the gas generating system comprising sodium bicarbonate and citric acid were dry granulated. To this the lubricant magnesium stearate was added and mixed thoroughly and then compressed into tablet 13 mm in diameter. The composition of the gastroretentive tablet is given in Table 32.

TABLE 32

Composition of ofloxacin gastroretentive tablet

| Tablet Composition | Weight (mg) |
|---|---|
| Ofloxacin | 250.00 |
| pH dependent graft copolymer | 75.00 |
| Gellable polymer | 100.00 |
| Sodium bicarbonate | 35.00 |
| Citric acid | 35.00 |
| Magnesium stearate | 5.00 |
| Total | 500.00 |

(b) Dissolution of Ofloxacin

The dissolution of ofloxacin was monitored using a USP dissolution apparatus and paddle method at 50 rpm. The dissolution medium was 0.1 N HCL and the temperature was maintained at 37±0.5° C. A known volume of releasing solution was collected at predetermined intervals and analyzed for drug concentration. The tablet swelled in the release medium upon floating and retained its integrity for the entire duration over which the drug is released from the dosage form. The cumulative percent dissolution of the drug is summarized in the Table 33.

TABLE 33

Dissolution of ofloxacin

| Time (hours) | | | | | | | |
|---|---|---|---|---|---|---|---|
| 1.0 | 2.0 | 3.0 | 4.0 | 5.0 | 6.0 | 7.0 | 8.0 |
| % Dissolved (Cumulative) | | | | | | | |
| 15.09 | 22.30 | 29.71 | 36.13 | 42.15 | 51.03 | 54.30 | 57.36 |

| Time (hours) | | | | | | | |
|---|---|---|---|---|---|---|---|
| 9.0 | 10.0 | 11.0 | 12.0 | 13.0 | 14.0 | 15.0 | 16.0 |
| % Dissolved (Cumulative) | | | | | | | |
| 61.51 | 66.15 | 69.11 | 72.66 | 75.13 | 78.29 | 80.86 | 84.02 |

We claim:

1. A gastroretentive, extended release composition for oral administration comprising:
   a. a graft copolymer of formula 1 which exhibits pH dependent behavior and capable of swelling at acidic pH, represented by

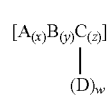

Formula 1 wherein the said graft copolymer comprises:
   I. a backbone having the formula $[A_{(x)} B_{(y)} C_{(z)}]$ comprising:
      a diol (A) selected from the group consisting of 1,2-ethane diol, 1,3-propane diol, 1,2-propane diol, 2-methyl-1,3-propane diol, 1,4-butane diol, 1,3-butane diol, 1,2-butane diol, 1,5-pentane diol, 1,6-hexane diol, 1,7-heptane diol, 1,8-octane diol, 1,9-nonane diol, 1,12-dodecane diol, 1,4-cyclohexanedimethanol and bis(2-hydroxyethyl)terephthalate,
      a dicarboxylic acid (B) selected from the group consisting of succinic acid, glutaric acid, adipic acid, pimelic acid, suberic acid, azelaic acid, sebacic acid, and dodecanedioic acid or acid anhydride (B) selected from the group consisting of succinic anhydride and phthalic anhydride and
      an epoxy monomer (C) containing pendant unsaturation selected from the group consisting of glycidyl methacrylate and glycidyl acrylate or a diol monomer (C) containing pendant unsaturation selected from the group consisting of trimethylolpropane monomethacrylate and trimethylolpropane monoacrylate,
      wherein (x)=41-45%, (y)=49-53% (z)=4-7% by mole; and
   II. a graft which is a polymer of a vinyl pyridine monomer (D) and 'w' is a weight percent of the total weight of said graft copolymer such that 'w' is 22-52%;
   b. a gellable polymer, said gellable polymer selected from the group consisting of cellulosic polymers and polyalkene oxide;
   c. a therapeutically active agent;
   d. a gas generating system, said gas generating system comprising a gas generating agent and a carboxyl compound, said gas generating agent selected from the group consisting of alkali carbonates and bicarbonates; and
   e. pharmaceutically acceptable ingredients.

2. The gastroretentive, extended release composition as claimed in claim 1, wherein the backbone is an unsaturated polyester.

3. The gastroretentive, extended release composition as claimed in claim 1, wherein the vinyl pyridine monomer is selected from the group consisting of 2-vinyl pyridine, 3-vinyl pyridine and 4-vinyl pyridine.

4. The gastroretentive, extended release composition as claimed in claim 1, wherein the vinyl pyridine monomer is 4-vinylpyridine.

5. The gastroretentive, extended release composition as claimed in claim 1, wherein the pH dependent graft copolymer comprises 20-40% of the total weight of the composition.

6. The gastroretentive, extended release composition as claimed in claim 1, wherein the gellable polymer is selected from the group consisting of hydroxypropylmethyl cellulose, hydroxyethyl cellulose, and polyethylene oxide.

7. The gastroretentive, extended release composition as claimed in claim 1, wherein the gellable polymer comprises 20-40% of the total weight of the composition.

8. The gastroretentive, extended release composition as claimed in claim 1, wherein the therapeutically active agent is selected from the group consisting of antibiotic drugs, cardiovascular drugs and vitamins.

9. The gastroretentive, extended release composition as claimed in claim 8, wherein the antibiotic drug is selected from the group consisting of ciprofloxacin, ampicillin, ofloxacin, amoxicillin and cephalexin.

10. The gastroretentive, extended release composition as claimed in claim 8, wherein the cardiovascular drug is selected from the group consisting of verapamil, nifedepine, captopril, propranolol, atenolol and diltiazem.

11. The gastroretentive, extended release composition as claimed in claim 8, wherein vitamin is selected from the group consisting of thiamine hydrochloride, riboflavin 5'-phosphate sodium, pyridoxine hydrochloride and L-(+)-ascorbic acid.

12. The gastroretentive, extended release composition as claimed in claim 1, wherein the therapeutically active agent comprises 10-50% of the total weight of the composition.

13. The gastroretentive, extended release composition as claimed in claim 1, wherein the gas generating agent is selected from the group consisting of sodium carbonate, calcium carbonate, sodium bicarbonate and potassium bicarbonate.

14. The gastroretentive, extended release composition as claimed in claim 1, wherein the carboxyl compound is selected from the group consisting of malic acid, fumaric acid, tartaric acid, citric acid and ascorbic acid.

15. The gastroretentive, extended release composition as claimed in claim 1, wherein the gas generating system comprises 12-18% of the total weight of the composition.

16. The gastroretentive, extended release composition as claimed in claim 1, wherein the gastroretentive, extended release composition is produced in pharmaceutical solid dosage form.

* * * * *